United States Patent
Jacobs (10) Patent No.: US 6,893,452 B2
(45) Date of Patent: May 17, 2005

(54) MULTI-POINT TENSION DISTRIBUTION SYSTEM DEVICE AND METHOD OF TISSUE APPROXIMATION USING THAT DEVICE TO IMPROVE WOUND HEALING

(75) Inventor: Daniel Jacobs, Palo Alto, CA (US)

(73) Assignee: Coapt Systems, Inc., Palo Alto, CA (US)

( * ) Notice: Subject to any disclaimer, the term of this patent is extended or adjusted under 35 U.S.C. 154(b) by 151 days.

(21) Appl. No.: 10/140,897

(22) Filed: May 6, 2002

(65) Prior Publication Data

US 2002/0173807 A1 Nov. 21, 2002

Related U.S. Application Data

(63) Continuation of application No. 09/574,603, filed on May 19, 2000, now Pat. No. 6,645,226.

(51) Int. Cl.[7] .................................. A61B 17/08
(52) U.S. Cl. .......................................... 606/215
(58) Field of Search ......................... 606/215, 213, 606/216, 230, 214, 157, 151, 232, 233

(56) References Cited

U.S. PATENT DOCUMENTS

| | | |
|---|---|---|
| 2,421,193 A | 5/1947 | Gardner |
| 2,472,009 A | 5/1949 | Gardner |
| 3,031,730 A | 5/1962 | Mori |
| 3,471,903 A | 10/1969 | Northrup et al. |
| 3,646,615 A | 3/1972 | Ness |
| 3,914,144 A | 10/1975 | Ribich et al. |
| 3,973,277 A | 8/1976 | Semple et al. |
| 3,981,051 A | 9/1976 | Brumlik |
| 4,259,959 A | 4/1981 | Walker |
| 4,430,998 A | 2/1984 | Harvey et al. |
| 4,535,772 A | 8/1985 | Sheehan |
| 4,610,250 A | 9/1986 | Green |
| 4,651,724 A | 3/1987 | Berentey et al. |
| 4,865,026 A | 9/1989 | Barrett |
| 4,960,420 A | 10/1990 | Goble et al. |
| 4,979,956 A | 12/1990 | Silvestrini |
| 5,047,047 A | 9/1991 | Yoon |
| 5,108,422 A | 4/1992 | Green et al. |
| 5,176,692 A | 1/1993 | Wilk et al. |
| 5,179,964 A | 1/1993 | Cook n |

(Continued)

FOREIGN PATENT DOCUMENTS

| | | |
|---|---|---|
| FR | 2 744 623 | 8/1997 |
| WO | WO 00/49983 | 8/2000 |
| WO | WO 01/89392 A2 A3 | 11/2001 |
| WO | PCT/US03/18753 | 6/2003 |

OTHER PUBLICATIONS

Dialog English abstract of French patent publication No. 2 744 623 published on Aug. 14, 1997, one page, located in Derwent file 351 on Mar. 25, 2002.

U.S. Appl. No. 10/170, 530, filed Jun. 12, 2002, Jacobs et al.
U.S. Appl. No. 09/816,641, filed Feb. 22, 2001, Jacobs et al.
U.S. Appl. No. 10/418,325, filed Apr. 17, 2003, Jacobs et al.
U.S. Appl. No. 10/418,541, filed Apr. 17, 2003, Jacobs.
U.S. Appl. No. 10/246,174, filed Sep. 17, 2002, Jacobs et al.

Primary Examiner—Kevin T. Truong
(74) Attorney, Agent, or Firm—DLA Piper Rudnick Gray Cary US LLP (57) ABSTRACT

A tissue approximation device and processes for using the device are provided. The device is an implantable, biodegradable construct (except for hernia repairs) that has attachment points emanating from a supportive backing. The device improves the mechanical phase of wound healing and evenly distributes tension over the contact area between the device and tissue. Processes for using the device include wound closure, vascular anastomoses, soft tissue attachment and soft tissue to bone attachment.

27 Claims, 13 Drawing Sheets

U.S. PATENT DOCUMENTS

| | | |
|---|---|---|
| 5,254,127 A | 10/1993 | Wholey et al. |
| 5,263,973 A | 11/1993 | Cook |
| 5,281,422 A | 1/1994 | Badylak et al. |
| 5,342,395 A | 8/1994 | Jarrett et al. |
| 5,352,229 A | 10/1994 | Goble et al. |
| 5,383,897 A | 1/1995 | Wholey |
| 5,425,747 A | 6/1995 | Brotz |
| 5,531,760 A | 7/1996 | Alwafaie |
| 5,531,790 A | 7/1996 | Frechet et al. |
| D374,286 S | 10/1996 | Goble et al. |
| 5,569,272 A | 10/1996 | Reed et al. |
| 5,571,104 A | 11/1996 | Li |
| 5,571,216 A | 11/1996 | Anderson |
| 5,584,859 A | 12/1996 | Brotz |
| 5,591,203 A | 1/1997 | Fahy |
| 5,598,610 A | 2/1997 | Torigoe et al. |
| 5,611,814 A | 3/1997 | Lorenc |
| 5,662,714 A | 9/1997 | Charvin et al. |
| 5,723,009 A | 3/1998 | Frechet et al. |
| 5,779,706 A | 7/1998 | Tschakaloff |
| 5,785,713 A | 7/1998 | Jobe |
| 5,868,746 A | 2/1999 | Sarver et al. |
| 5,906,617 A | 5/1999 | Meislin |
| 5,916,224 A | 6/1999 | Esplin |
| 5,919,234 A | 7/1999 | Lemperle et al. |
| 5,925,078 A | 7/1999 | Anderson |
| 5,931,840 A | 8/1999 | Goble et al. |
| 5,941,878 A | 8/1999 | Medoff |
| 5,950,633 A | 9/1999 | Lynch et al. |
| 5,954,747 A | 9/1999 | Clark |
| 5,961,520 A | 10/1999 | Beck et al. |
| 5,968,097 A | 10/1999 | Frechet et al. |
| 5,984,927 A | 11/1999 | Wenstrom, Jr. et al. |
| 5,984,949 A | 11/1999 | Levin |
| 6,015,410 A | 1/2000 | Törmälä et al. |
| 6,039,741 A | 3/2000 | Meislin |
| 6,066,159 A | 5/2000 | Bergstrom |
| 6,080,192 A | 6/2000 | Demopulos |
| 6,083,244 A | 7/2000 | Lubbers et al. |
| 6,106,544 A | 8/2000 | Brazeau |
| 6,106,556 A | 8/2000 | Demopulos et al. |
| 6,132,442 A | 10/2000 | Ferragamo et al. |
| 6,165,203 A | 12/2000 | Krebs |
| 6,168,596 B1 | 1/2001 | Wellisz et al. |
| 6,168,633 B1 | 1/2001 | Shoher et al. |
| 6,235,058 B1 | 5/2001 | Huene |
| 6,267,772 B1 | 7/2001 | Mulhauser et al. |
| 6,270,517 B1 | 8/2001 | Brotz |
| 6,296,641 B2 | 10/2001 | Burkhead et al. |
| 6,328,743 B2 * | 12/2001 | Lerch .......................... 606/215 |
| 6,350,284 B1 | 2/2002 | Tormala et al. |
| D462,766 S | 9/2002 | Jacobs et al. |
| 6,482,232 B1 | 11/2002 | Boucher et al. |
| 6,485,493 B1 * | 11/2002 | Bremer ....................... 606/215 |
| 6,485,503 B2 | 11/2002 | Jacobs et al. |
| 6,645,226 B1 | 11/2003 | Jacobs et al. |
| 6,712,830 B2 | 3/2004 | Esplin |
| 2001/0021875 A1 | 9/2001 | Enzerink et al. |
| 2002/0022861 A1 | 2/2002 | Jacobs et al. |

* cited by examiner

MULTI-POINT TENSION DISTRIBUTION SYSTEM DEVICE AND METHOD OF TISSUE APPROXIMATION USING THAT DEVICE TO IMPROVE WOUND HEALING

CROSS-REFERENCE TO RELATED APPLICATIONS

This is a continuation of U.S. patent application Ser. No. 09/574,603 entitled "Multi-Point Tension Distribution System Device And Method Of Tissue Approximation Using That Device To Improve Wound Healing" filed May 19, 2000, now U.S. Pat. No. 6,645,226 and incorporated herein by reference in its entirety.

FIELD OF THE INVENTION

This invention is in the field of surgery. More particularly, it relates to a tissue approximation device that facilitates wound healing by holding soft tissue together under improved distribution of tension and with minimal disruption of the wound interface and its nutrient supplies. The device has multiple sites for grasping said tissue using tines or prongs or other generally sharp, projecting points, extending from a single, supportive backing. Various processes of using the inventive device are also a portion of the invention.

BACKGROUND OF THE INVENTION

The surgically induced healing of soft tissue wounds involves two phases, the mechanical phase of wound closure followed by the biochemical phase which involves protein bridging and scarring. In the mechanical phase, the edges of soft tissue are held in contact by essentially two components: 1) The physical properties and device-tissue interactions of the materials holding the tissue edges in contact, e.g. sutures or staples; and 2) An early deposition of proteinaceous material that has adhesive characteristics, e.g. fibrin glue.

Only in the biochemical phase, which occurs after the mechanical phase, do tissue components replace the mechanical components adhering the wound surfaces. During the biochemical phase, the inflammatory cascade generates signals which induce fibroblasts to migrate into the wound and synthesize collagen fibers.

Collagen is the primary constituent of connective tissue and ultimately determines the pliability and tensile strength of the healing wound. Tensile strength is gradually recovered; 60% of ultimate wound strength is achieved after approximately 3 months. However, this process is successful only if the previous mechanical phase has proceeded normally.

The surgeon's goal is to optimize the strength and often the cosmetic appearance of a wound closure or tissue coaptation. For this to happen, tissue is mechanically approximated until the wound has healed enough to withstand stress without artificial support. Optimal healing requires the application of appropriate tissue tension on the closure to eliminate dead space but not create ischemia within the tissue. Both of these circumstances increase the risk of wound infection and wound dehiscence.

Although the biomaterial composition of sutures has progressed considerably, the sophistication of manual suture placement in wounds has advanced relatively little since the original use of fabrics several thousand years ago to tie wound edges together. The wide tolerance ranges for suture placement, tension, and configurations, both amongst different surgeons and for different implementations by the same surgeon, result in a significant component of sub-optimal technique. Yet, the technique used for wound closure forms the foundation for all subsequent events in the healing process. It is during this mechanical phase that tissue tension is high, edema and inflammation are intense, wound edge ischemia is greatest, and that one can already observe the complication of wound failure.

Soft tissue is well known for its inability to hold tension. Even when optimally placed, sutures gradually tear through soft tissue, producing gaps in wounds and possibly leading to the eventual failure or sub-optimization of wound healing. Furthermore, since sutures require the implementation of high levels of tension to counteract the forces acting to separate tissues, they may strangulate the blood supply of the tissues through which they are placed, thus inhibiting the delivery of wound nutrients and oxygen necessary for healing.

There have been many attempts to construct wound closure devices that decrease closure time and improve cosmesis. U.S. Pat. Nos. 2,421,193 and 2,472,009 to Gardner; U.S. Pat. No. 4,430,998 to Harvey et al.; U.S. Pat. No. 4,535,772 to Sheehan; U.S. Pat. No. 4,865,026 to Barrett; U.S. Pat. No. 5,179,964 to Cook; and U.S. Pat. No. 5,531,760 to Alwafaie suggest such devices. However, these devices are not useful in surgical or deeper wounds. They only approximate the skin surface, joining skin edges variously through external approaches, using adhesives or non-absorbable attachment points that penetrate tissue. The devices minimally improve the biomechanics of wound closure, and do not adequately approximate the deeper layers of the closure, i.e. fascia or dermis. Externally placed attachment points that puncture the skin lateral to the wound also interfere with long-term cosmesis and provide a possible conduit for infecting microorganisms.

U.S. Pat. No. 5,176,692 to Wilk et al., discloses a device for hernia repair that utilizes mesh with pin-like projections to cover hernia defects. This device, however, is used in a laparoscopic hernia repair in conjunction with an inflatable balloon. Closure devices for deeper tissues are described in U.S. Pat. No. 4,610,250 to Green; U.S. Pat. No. 5,584,859 to Brozt et al.; and U.S. Pat. No. 4,259,959 to Walker. However, these devices either work in conjunction with sutures, are made of materials that do not suggest biodegradability, or are designed in such a way as not to impart uniform tension on the closure, increasing the risk of wound separation and failure of wound healing.

The present invention is a biodegradable tissue approximation device. The device includes a plurality of attachment points, e.g. tines, prongs, or other generally sharp or blunt parts, connected to a backing that can be manipulated to close wounds, join soft tissue or bone, or create anastomoses. This multi-point tension distribution system (MTDS) device may be placed with minimal tissue trauma. The present invention typically incorporates the deeper layers of tissue within the closure, and the multiple attachment points distribute the resulting tension, often uniformly. Approximation from the internal aspect of the wound minimizes the potential for dead space in the closure, thus decreasing the risk of sub-optimal healing. Moreover, because the device is absorbed, a second procedure is not typically needed to remove the device.

Thus, the present invention improves the mechanical phase of healing by facilitating wound closure and/or the coaptation of tissues prior to initiation of the biochemical phase of wound healing. Placement of the device maximizes the chance for a good cosmetic result and is not heavily dependent on surgeon skill. Closure time is also shortened, decreasing overall cost and risk of operative complications.

SUMMARY OF THE INVENTION

The present invention is a device that improves the mechanical phase of wound healing. In the preferred embodiment, tissue edges are stabilized by a plurality of attachment points that extend from a supportive backing. The density, shape, length, and orientation of attachment points on the backing may be varied to suit the procedure, type of tissue being approximated, and/or area of the body involved. The flexibility of the backing is also variable and dependent on the materials used and dimensions of the backing. In the preferred embodiment, the device is biodegradable, and the attachment points uniformly distribute tension over the contact area between the device and tissue.

Processes of using the present invention are also provided. The device may be used to close wounds and create vascular anastomoses. The device may also be manipulated to approximate soft tissue and soft tissue to bone.

BRIEF DESCRIPTION OF THE DRAWINGS

FIGS. 11F–11G are side, schematic views.

DETAILED DESCRIPTION OF THE INVENTION

Figures 1A, 1B:
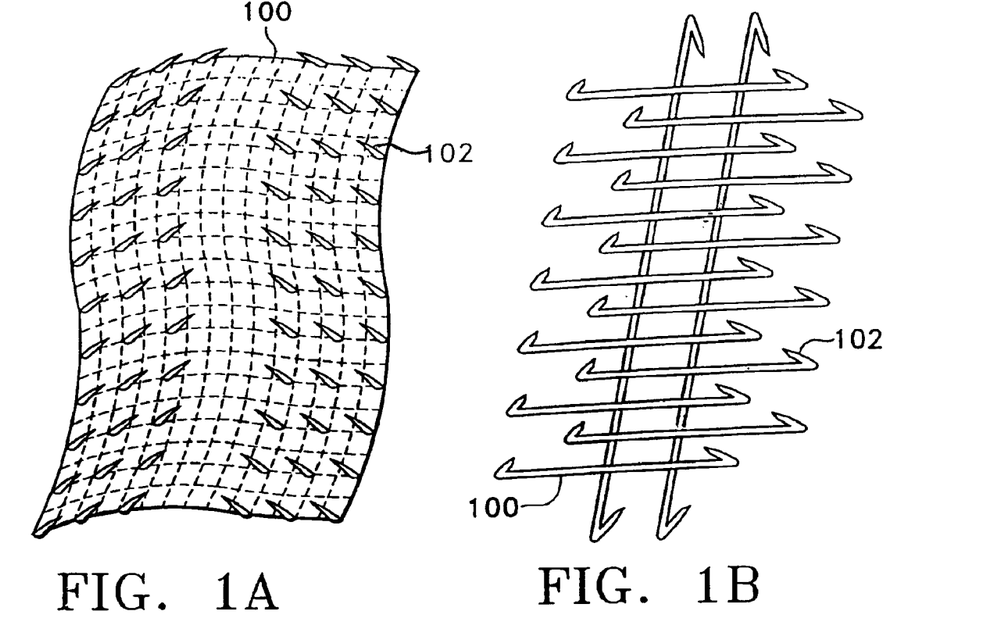
FIGS. 1A–1D are plan, perspective views of various MTDS devices.
Figures 1C, 1D:
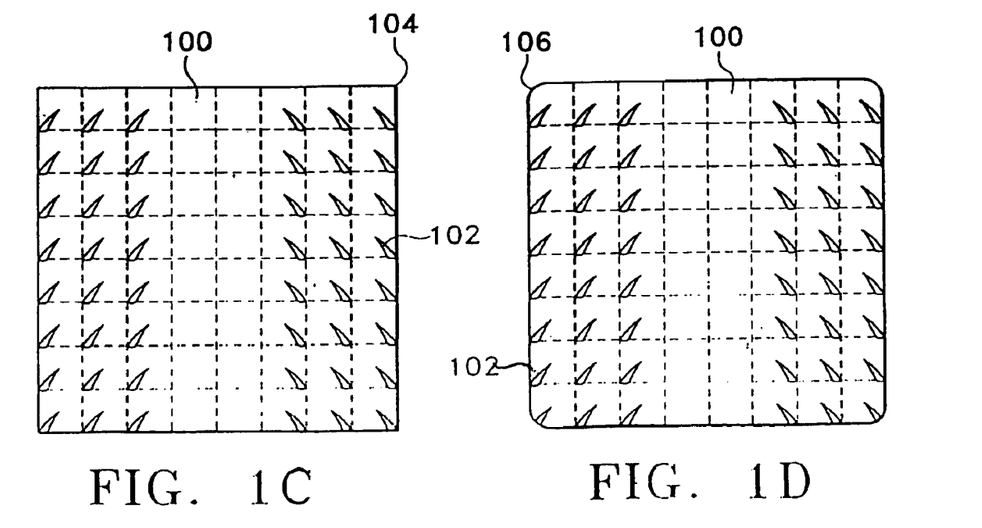
Figure 2A:
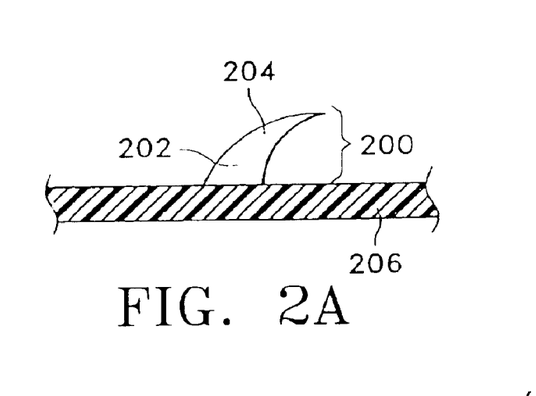
FIGS. 2A–2E are side views of various attachment point shapes and orientations.
Figure 2B:
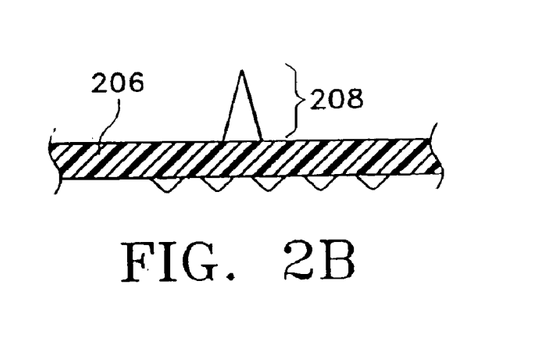
Figure 2C:
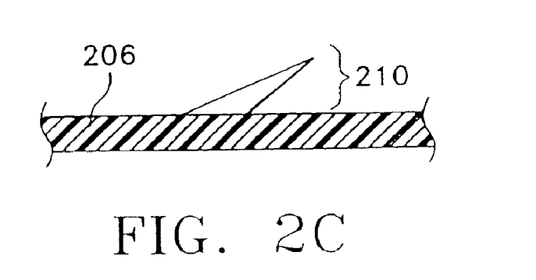
Figure 2D:
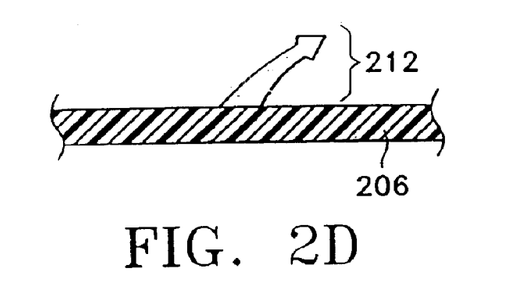
Figure 2E:
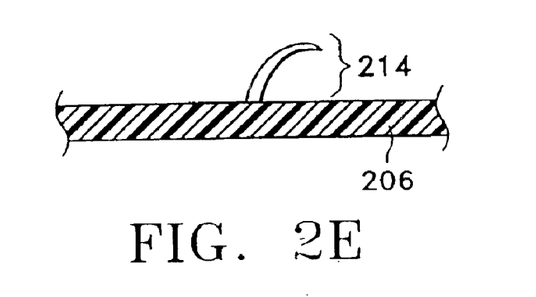

Our inventive device may be used when working with bone anchors or a variety of soft tissues. The device is of the general configurations shown in FIGS. 1A–1B and comprises a plurality of attachment points (102) emanating from a supportive backing (100) that is a generally a porous material that may have the structure of a mesh, net, or lattice. The degree of flexibility of the backing is determined by the material of construction, the shape and dimensions of the device, the type and properties of the approximated tissue, and the area of the body into which the device is placed. For example, a tightly curved or mobile part of the body, e.g. a joint, will require a more flexible backing, as would a tendon or nerve repair due to the amount of bending the device needs for the attachment. Also, depending on the type of material used, the thickness of the backing as well as its width and length may determine the flexibility of the device. Furthermore, the backing may be pre-fabricated into different shapes as shown by the sharp corners (104) and rounded corners (106) in FIGS. 1C and 1D. The fabricated cross-sectional shape and dimensions of the mesh elements may vary to promote flexibility in regions of the backing. The cross-sectional shape of the mesh elements may be chosen to minimize local compressive stress between the backing and surface it rests upon, or have rounded and filleted edges to be less obtrusive to local circulation. The plurality of attachment points distribute tension over the contact area between the device and the tissue.

Materials such as biodegradable polymers are preferably used to construct the backing and attachment points. Polymers synthesized from monomers comprising esters, anhydrides, orthoesters, and amides are particularly suitable for biodegradation. Examples of biodegradable polymers are polyglycolide, polylactide, poly-α-caprolactone, polydiaxanone, polyglyconate, polylactide-co-glycolide, and block and random copolymers of these polymers. Copolymers of glycolic, lactic, and other α-hydroxy acids are highly desirable. Although we prefer to use a single polymer or copolymer in a specific device, generally for ease of construction, the invention is not so limited. An example of an inventive device may be made of two or more types of polymers or copolymers (or molecular weights of the same polymer or copolymer). For instance, the backing material might be produced from a more flexible polymer and the points or tines of a stiffer material. The inflammatory response to these polymers is minimal, and they have been safely used in suture materials, stents, drug delivery devices, orthopedic fixation devices, and intestinal anastomotic rings.

Generally, we will refer to the attachment points as "tines" or "prongs". These tines will refer both to points which are either sharp, i.e. able to separate tissue in a chosen use, or blunt, i.e. not able to separate tissue in that use. The attachment points may also be referred to as "barbs" when those points have the retaining point shown in several of the Figures discussed below.

Figure 3A:
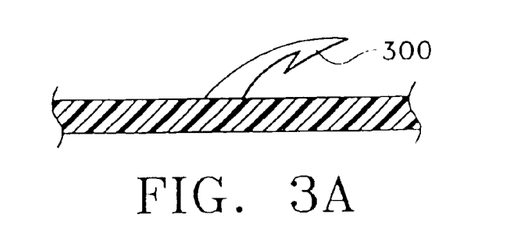
FIGS. 3A–3D and 3F–3G are side views of various attachment points.
Figure 3B:
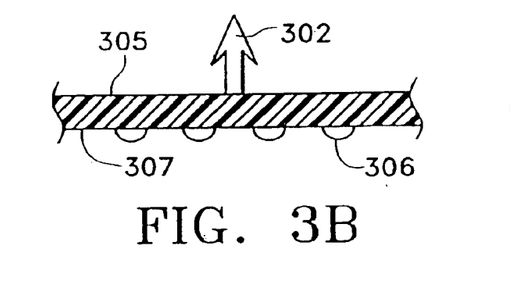
Figure 3C:
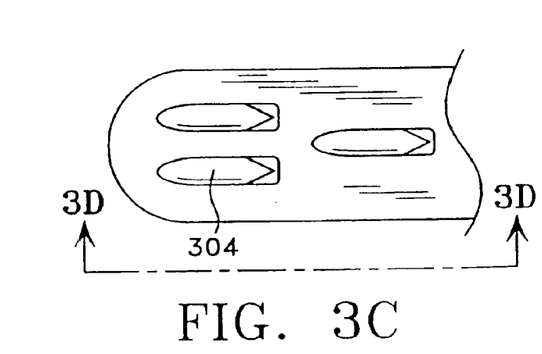
Figure 3D:
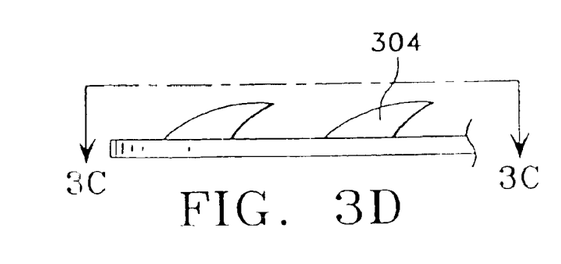

As shown in FIGS. 2A–2E, the shape of the attachment points or barbs may be varied depending, e.g., on the area of the body involved and the type of tissue requiring closure or reapproximation. The tines may be canted or erect, but in a preferred variation, the general structure of the tines is of a rose thorn shape. The tines (200) have a wide base (202) that supports a projection (204) from the backing (206) against the degree of tension required to close a wound or approximate tissue. For example, the attachment points may be erect tine (FIG. 2B–208), canted tine (FIG. 2C–210), canted arrowhead (FIG. 2D–212), canted hook (FIG. 2E–214), or may have a single straight cross-section (FIGS. 3G–3H) that is nail-like, that does not vary over the length of the prong, for example, similar in shape to a nail or sharpened pencil. Furthermore, the tip of the attachment points may be varied as shown in FIGS. 3A–3D. The tips may be barbed (300), arrowhead (double-barb) (302), or cheese grater (304). A side view of the cheese grater tips is shown in FIG. 3D.

The connection of the prong to the backing may be rounded or filleted, or the backing built-up around the prong, to reduce structural stress concentrations. The backing or connecting structure may branch out away from the center, with each branch in turn branching to grapple tissue in a distributed fashion. All edges of the device may be smooth except where sharpness is needed at the tip of the prong to pierce into the tissue. Once the prongs pierce into the tissue, the tissue may become supported against the backing to minimize additional piercing or irritation by the prong tip. The device may be molded, stamped, machined, woven, bent, welded or otherwise fabricated to create the desired features and functional properties.

Figure 3E:
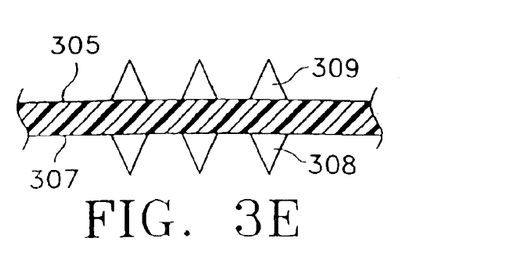
FIG. 3E is a side view of a two-sided MTDS device.
Figure 3F:
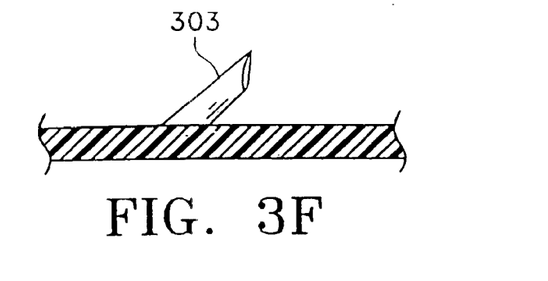
Figure 3G:
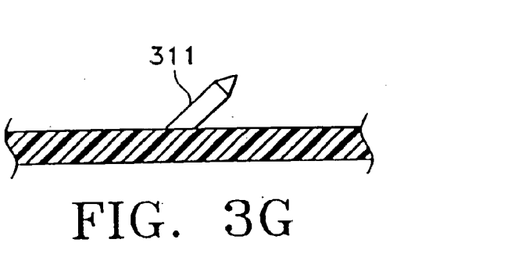
Figure 3H:
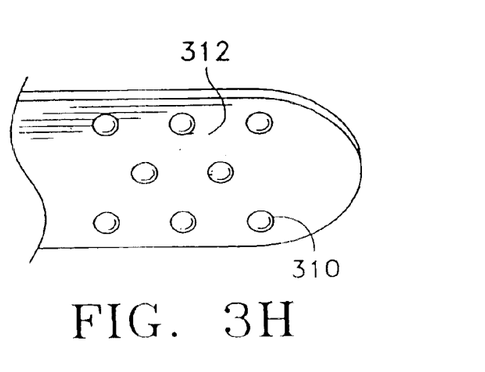
FIG. 3H is a plan, reverse perspective view of nubs on the inferior surface of a MTDS device.

The MTDS device may also have attachment points both on its front side (305) and on a back side (307). As shown in FIGS. 3B and 3E, the front and back sides have attachment points. The attachment points on the front side (309) generally approximate tissue. The attachment points on the back side (307) are auxiliary attachment points that may comprise forms such as round nubs (306) or pointed nubs (308). The auxiliary attachment points may be used to secure or promote stable implantation of the device. Soft tissue may be gently pressed into open regions of the backing thereby helping to fix the device in place against both underlying and overlying tissue. FIG. 3H shows a reverse view of the nubs (310) on the back side of the device (312). The attachment points on a two-sided device are not limited to the combinations disclosed above, but may comprise any combination of the previously mentioned attachment point shapes and orientations.

Figure 4A:
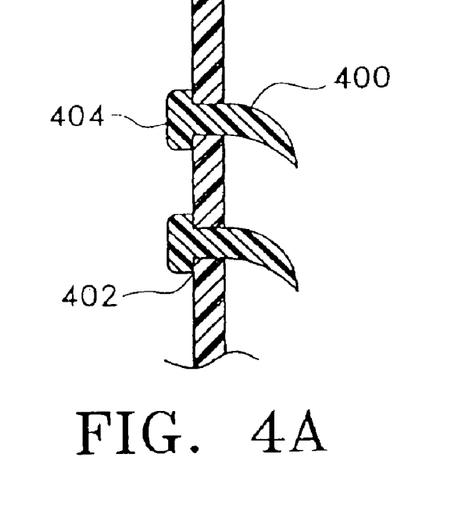
FIG. 4A is a side, cross-sectional view of attachment points that run through the width of a backing.
Figure 4B:
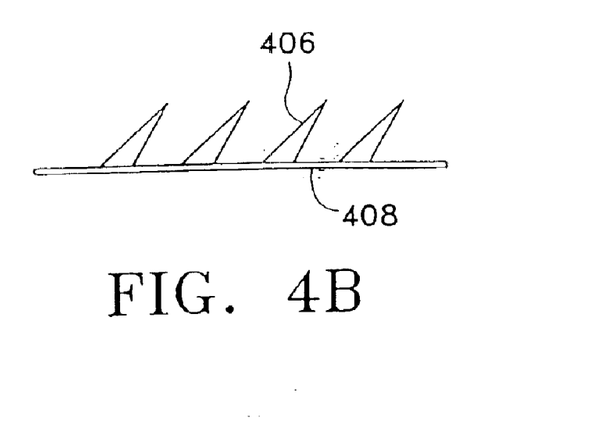
FIG. 4B is a side view of attachment points on a strip of backing material.
Figure 4C:
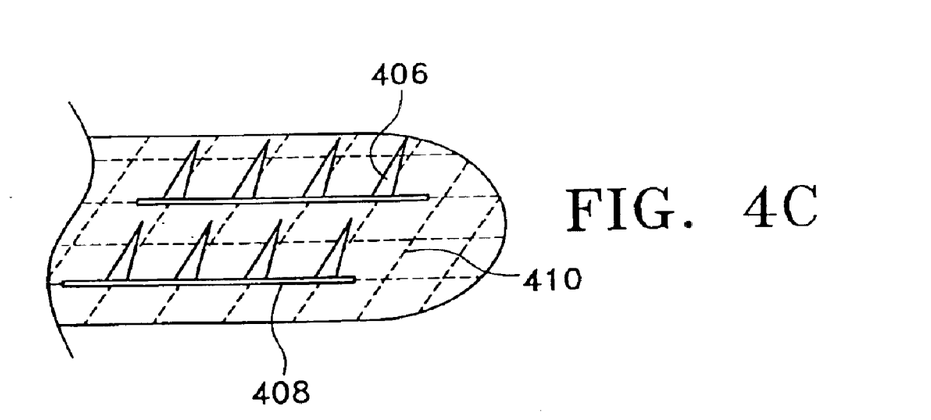
FIG. 4C is a plan, perspective view of the embodiment in 4B on a backing.
Figure 4D:
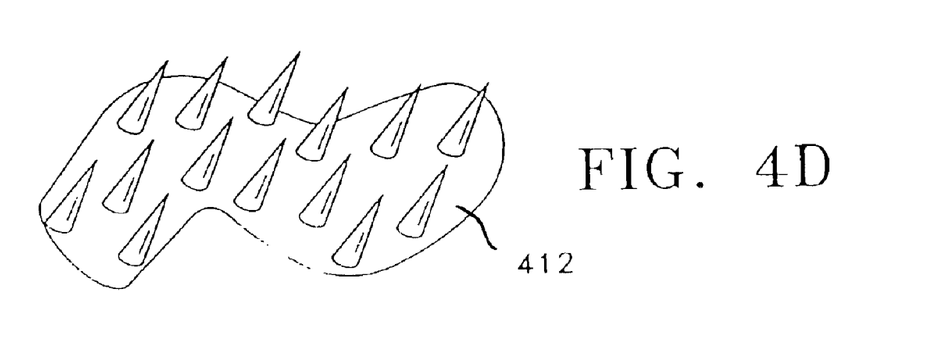
FIG. 4D is a plan, perspective view of attachment points on a solid backing.

Structural variations can also be made to the backing of the device. As shown in FIG. 4A, the attachment points (400) may be placed through a plurality of openings in the backing (402) and secured to the backing by a flange (404) or hub. In FIGS. 4B and 4C, the points (406) may also connect to strips (408) of the same material as the attachment points which are then secured to a backing (410). The backing may also be comprised of a solid material (412) instead of a porous material.

The extent of porosity, or total surface area may be used to control the absorption rate of the device, and may also be used to optimize the strength-to-mass properties of the device, increasing the section modulus of structural cross-sections per unit mass. The backing structure may comprise partial folds, waves or grooves to help hold tissue against both surfaces of the backing. Regions of the backing may function as suction cups to help hold tissue to the backing.

Figure 5A:
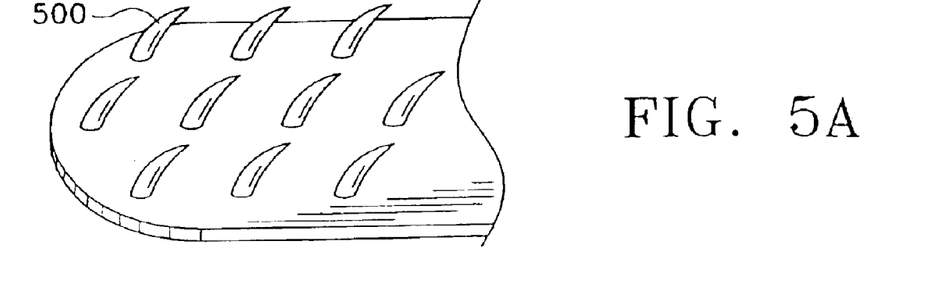
FIG. 5A is a plan, perspective view of attachment points canted in one direction.
Figure 5B:
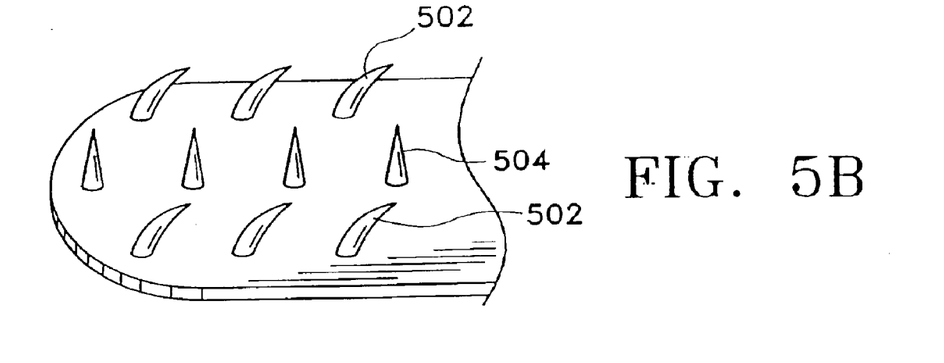
FIGS. 5B–5D are plan, perspective views of attachment points with various orientations on a backing.
Figure 5C:
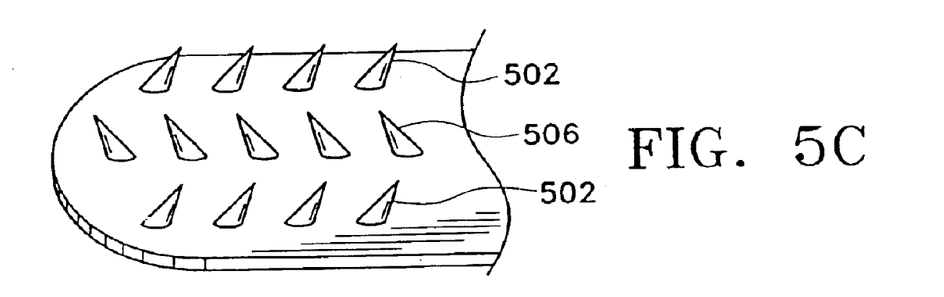
Figure 5D:
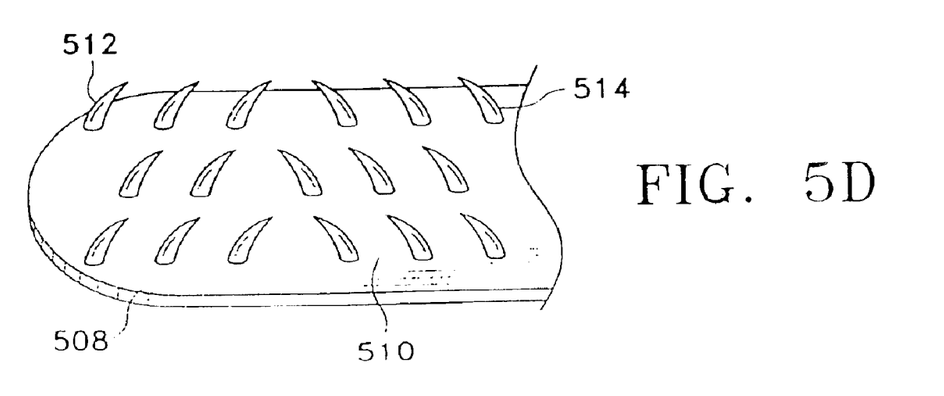

The density, distribution, length, and orientation of attachment points on the backing may be modified depending on the type of wound closure. Attachment points may be bent or curve gradually, with the tip directed at an optimal angle relative to the backing to aid device penetration and stability within the tissue, and to reduce tissue irritation after device installation. Attachment points may be canted in one direction (500), such as toward the center of the device as shown in FIG. 5A. The attachment points may also be variously oriented, such as toward center (502) and erect (504), or toward center (502) and away from center (506). It is within the scope of this invention to have attachment points extending in any relative direction or orientation on the backing. Or, as shown in FIG. 5D, the backing is divided into a first area (508) and a second area (510). Attachment points in the first area (512) and second area (514) are canted toward each other. The inventive device may also be sectioned into a plurality of areas, with each section being variously oriented to another section.

Figure 5E:
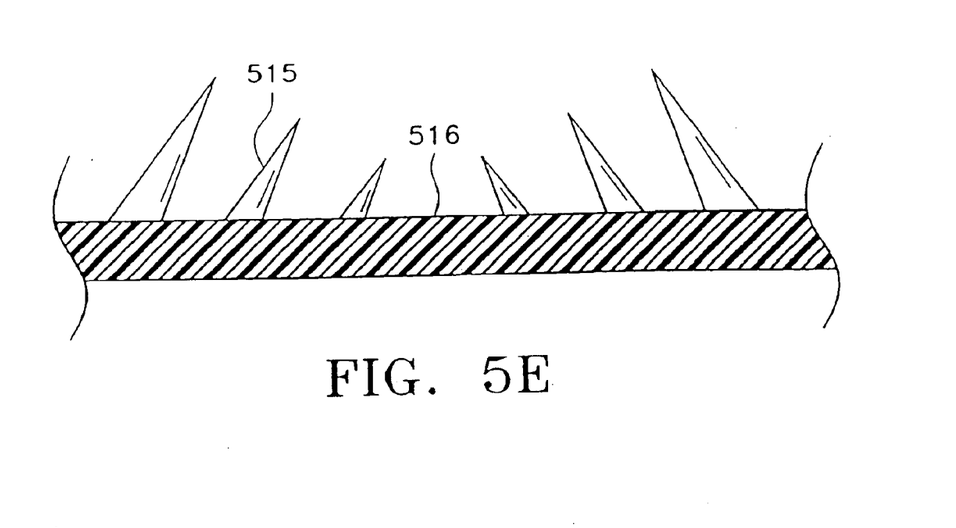
FIG. 5E is a side view of attachment points becoming progressively shorter the closer they are to the center of the device.
Figure 5F:
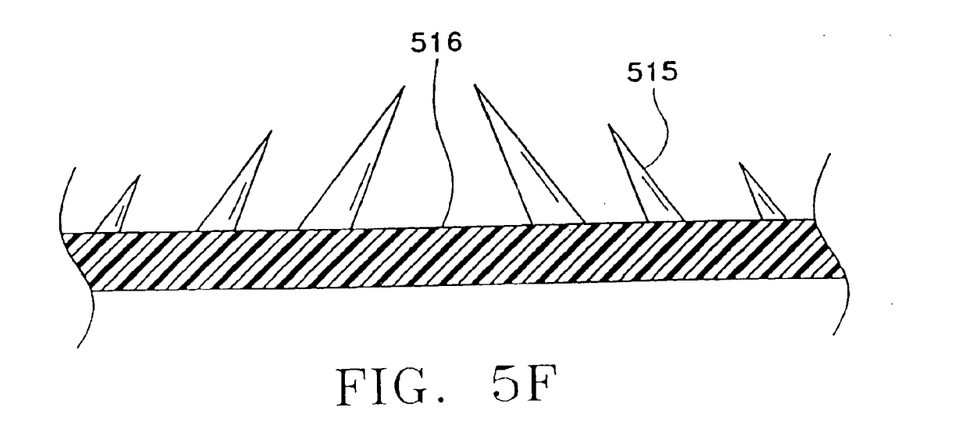
FIG. 5F is a side view of attachment points becoming progressively shorter the farther they are from the center of the device.

In another variation of the invention, attachment points of various lengths emanate from a single backing. For example, in FIG. 5E, the attachment points (515) are progressively shorter the closer they are to the center of the device (516). The attachment points (515) may also become progressively shorter the farther they are from the center of the device as shown in FIG. 5F. The variations shown in FIGS. 5B and 5C have regions of attachment points canted toward the center (502) and with other regions of attachment points with erect points (504 in FIG. 5B) or canted away from the other end (506 in FIG. 5C) of the device. These variations are more difficult to dislodge when situated in an area of the body having both to-and-fro movement, e.g., the inside of an elbow or back of the knee, or during placement of the device.

Figure 6A:
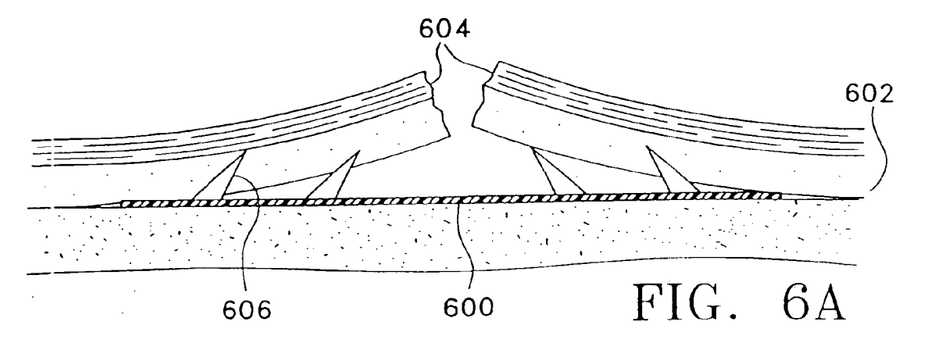
FIGS. 6A–6B are schematic views of a skin wound and wound repair using the MTDS device.
Figure 6B:
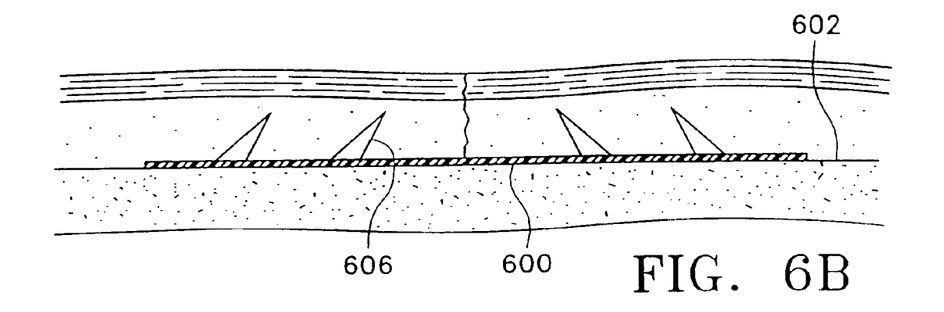
Figure 7:
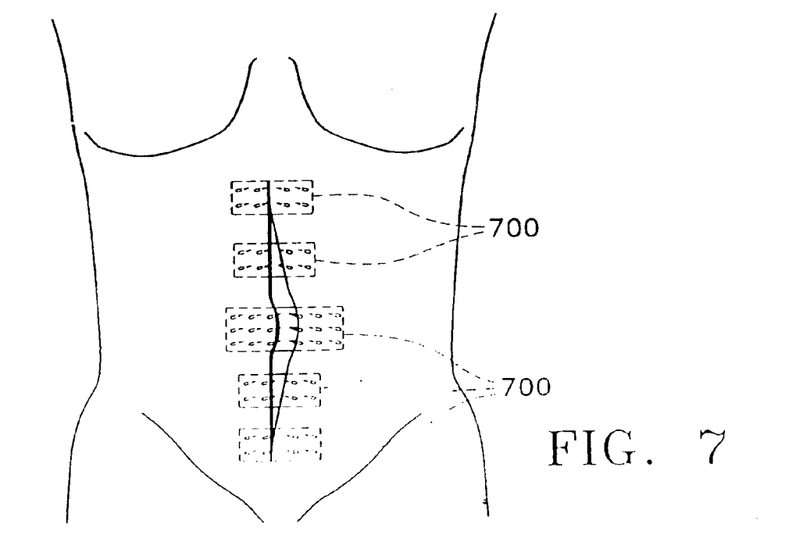
FIG. 7 is a schematic view of an abdominal wound closure using MTDS devices.

Portions of simple wound closures are shown in FIGS. 6A–6B. These wound closures involve placing the MTDS device (600) at the bottom of the wound, usually at the level of the sub-dermis (602). The edges of the wound (604) are approximated and then secured by fixation, e.g., by pressing, to the multiple attachment points (606). An example of the MTDS device placement in a laparotomy closure is shown in FIG. 7. The increased length of this incision requires placement of multiple devices (700).

Figure 8A:
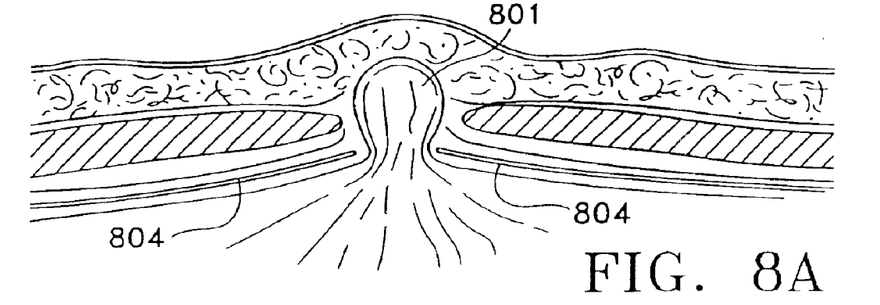
FIGS. 8A–8B are schematic views of an abdominal hernia and hernia repair using the MTDS device.
Figure 8B:
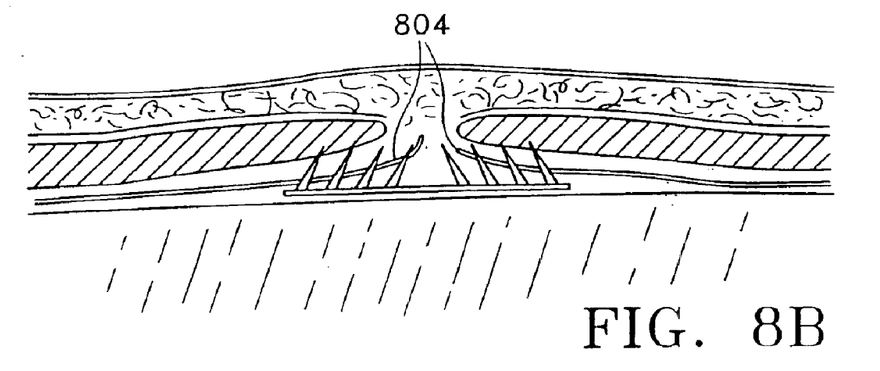
Figure 8C:
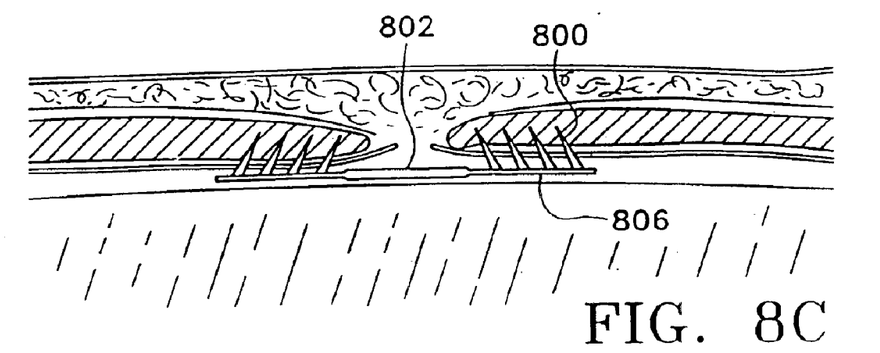
FIGS. 8C–8D are side and schematic views, respectively, of a MTDS device with attachment points on the edges of the backing and a central area without attachment points.
Figure 8D:
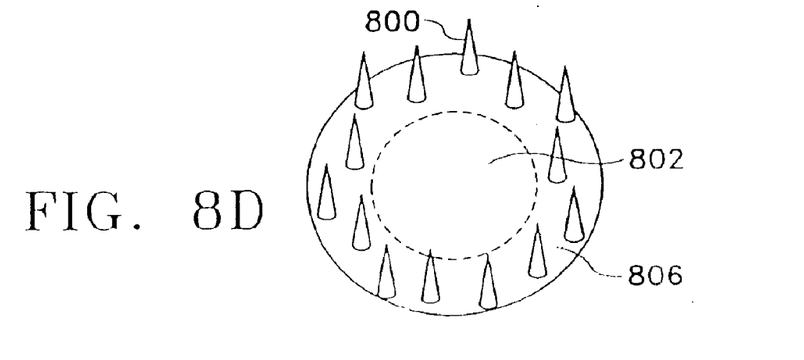

A unique application of this device occurs in hernia repair in which case the biomaterials are not absorbable but rather are more likely to be PTFE and POPU ("Gore-Tex"), polypropylene, or other permanent implant material. Once the hernia (801) is reduced, a MTDS device may be used to close the hernia defect by joining the edges of the separated fascia (804) as seen in FIGS. 8A and 8B. However, the device may also be modified to aid repair of a difficult hernia resulting from such circumstances as operating on an obese patient or large hernia, or having a wide fascial debridement where the fascial edges cannot be brought together. FIGS. 8C and 8D are variations of the inventive device that may be used in these cases. The attachment points (800) are secured to the ends of the backing (806) and are still used to adhere the device to tissue, but the points are spaced so that the central area of the backing is a flat surface without points (802) that covers the defect. The device in FIG. 8D is preferably used in an incisional hernia repair.

Figure 9A:
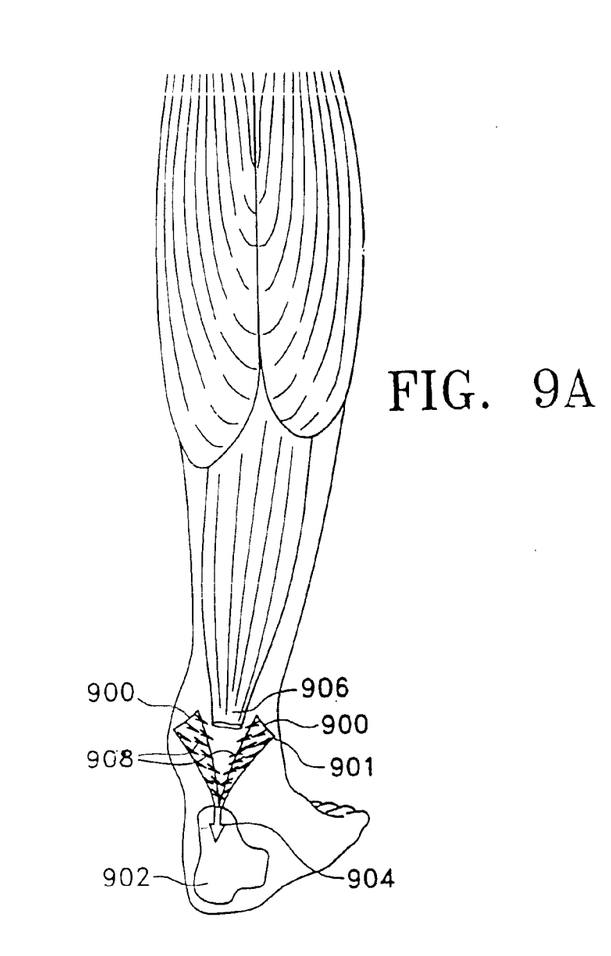
FIGS. 9A–9B are schematic views of a ruptured tendon and tendon to bone repair using the MTDS device.
Figure 9B:
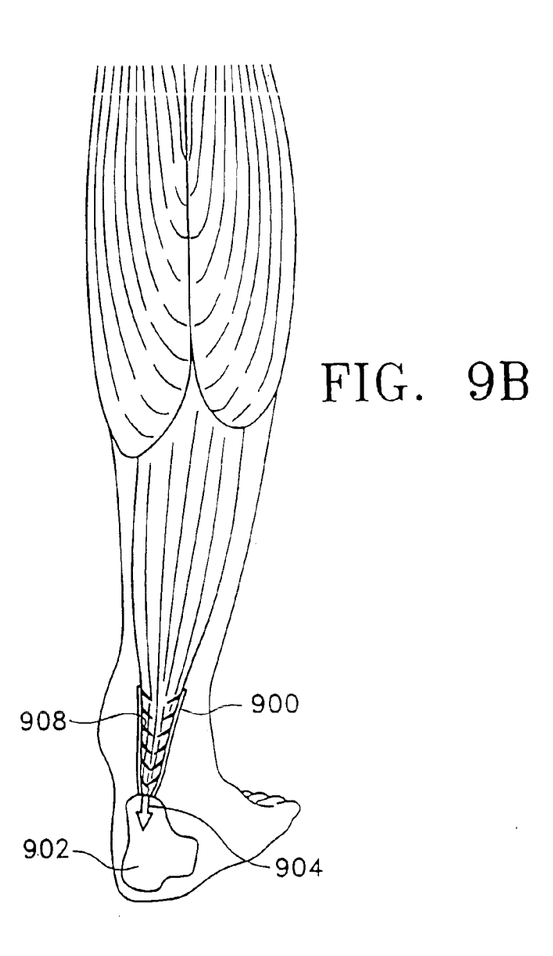

The MTDS device may also be constructed to reattach soft tissue such as tendons and ligaments to bone, as well as other soft tissue such as cartilage and the free ends of vessels or nerves. In FIG. 9A, the inventive device functions similar to a clamp. Backings with attachment points (900) are sides of a clamp that has a first end (901) and a second end (904). The first end (901) grasps tissue and the second end (904) is an anchor for tissue. For example, a ruptured tendon (906) may be fixed to the attachment points (908) of the first end of the clamp (901) and approximated to bone (902) with an anchor such as a pin or nail at the second end of the clamp (904), as seen in FIG. 9B. After mechanical fixation of the tissues, the biochemical phase of the wound healing process will begin, eventually forming a natural union between tendon and bone. Ligament and cartilage to bone unions using the MTDS device would undergo the same mechanical and biochemical processes.

Figure 10A:
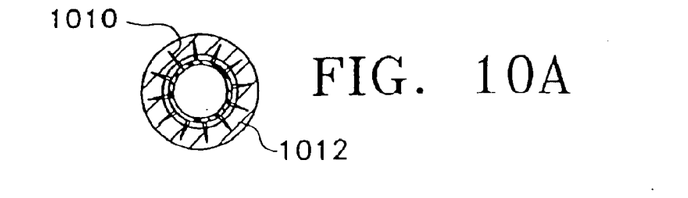
FIG. 10A is an axial view of a cross-section of a vessel repaired with the MTDS device.
Figure 10B:
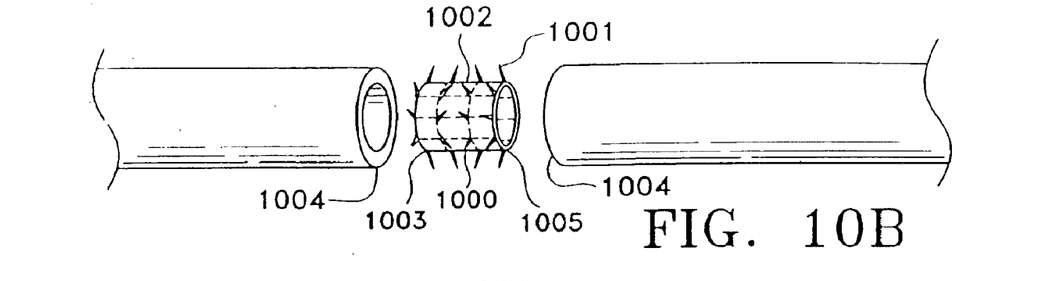
FIGS. 10B–10C are side, schematic views of vessel free ends and a vascular anastomosis using the MTDS device.
Figure 10C:
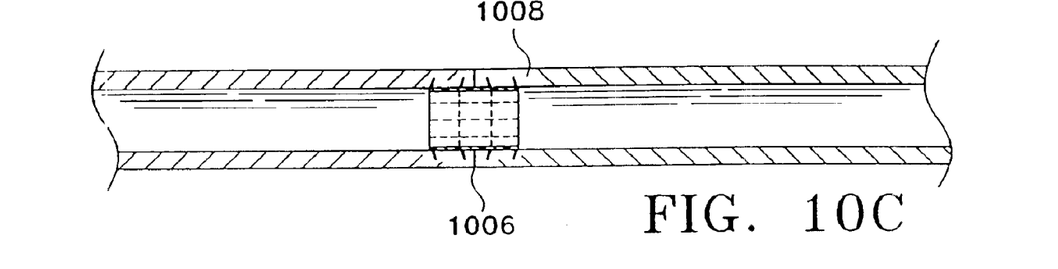

Vascular anastomoses may also be constructed with the MTDS device. In FIG. 10B, the backing has a tubular shape (1000) with attachment points (1001) on the outside surface (1002). The outside surface (1002) has a first end (1003) and a second end (1005) that opposes the first end (1003). The free ends of a vessel(s) (1004) are placed over the device, creating an anastomosis (1006) that is secured by attachment points fixed into the wall of the vessels (1008). The attachment points are preferably pointing towards the anastomosis (1006), with the attachment points on the first end (1003) being canted toward the second end (1005) and vice-versa. An axial view of the relationship of the attachment points (1010) to the vessel wall (1012) is shown in FIG. 10A.

Figure 11A:
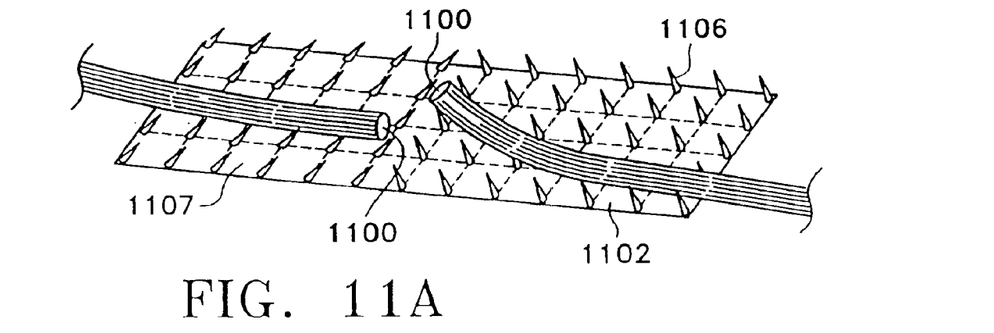
FIGS. 11A and 11B–11C are schematic, side, and cross-sectional side views, respectively, of a transected tendon and a tendon to tendon repair using the MTDS device.
Figure 11B:
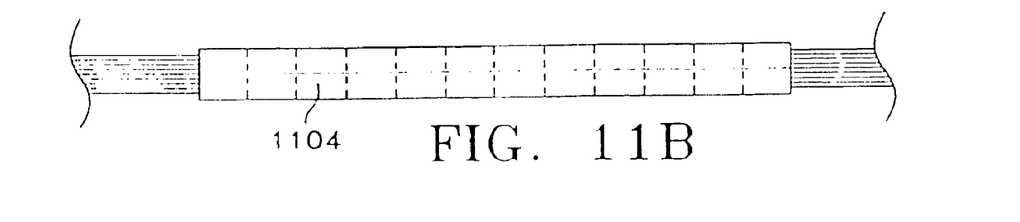
Figure 11C:
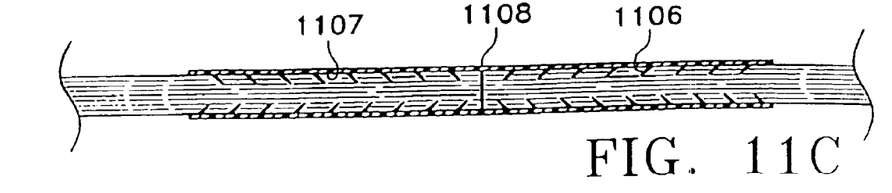
Figure 11D:
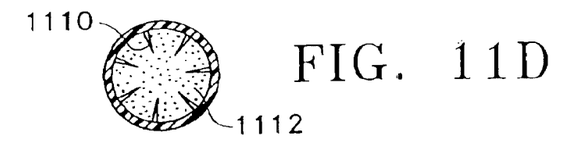
FIG. 11D is an axial, cross-sectional view of the MTDS tendon to tendon repair.
Figure 11E:
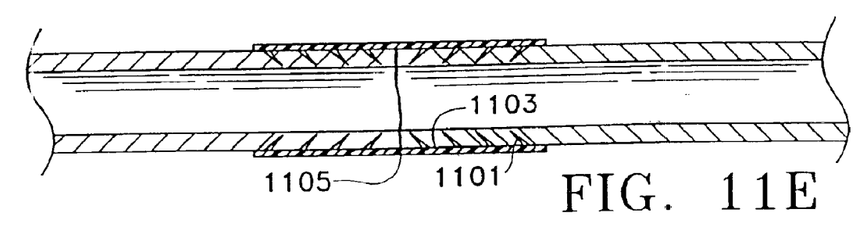
FIG. 11E is a side view of a vascular anastomosis using the MTDS device on the external surface of a vessel.
Figure 11F:
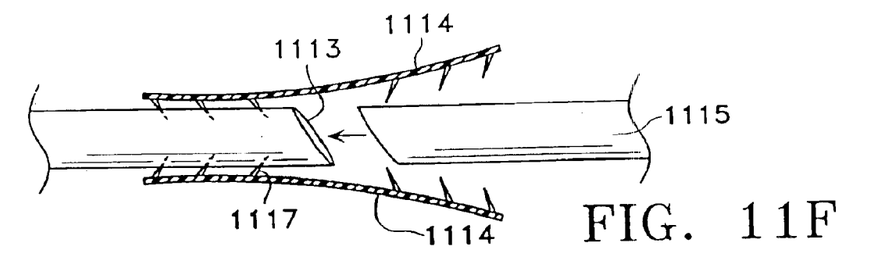
Figure 11G:
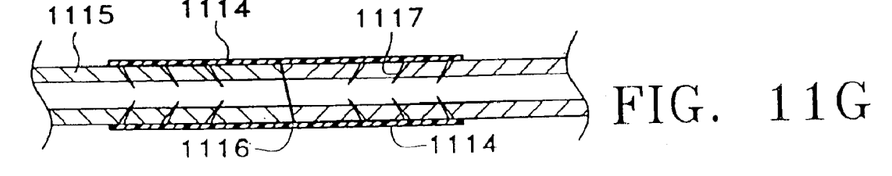
Figure 11H:
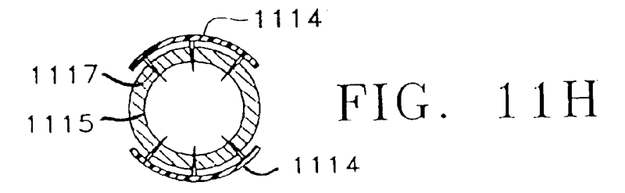
FIG. 11H is an axial view of the ends of a tubular structure being joined by externally placing strips of a MTDS device on approximated tissue.

Vessels and other soft tissue such as nerves, cartilage, tendons, and ligaments may also be joined as seen in FIGS. 11A and 11B. Two ends of tissue (1100) are brought and held together by the backing and attachment point construct (1102) being wrapped around the circumference of the tissue (1104). The attachment points (1106) are on the inside surface of the backing (1107) and secure the union at a central region (1108) as seen in FIG. 11C. An axial, cross-sectional view of the relationship between the attachment points (1110) and tissue (1112) is shown in FIG. 11D. The resulting form is, i.e., a tubular structure that has an inside surface (1107) with a central region (1108). The attachment points on the inside surface (1106) are canted toward the central region (1108). FIG. 11E shows the device with attachment points (1101) on the inside surface of the backing (1103) being wrapped around vessel ends to create an anastomosis (1105). Instead of being wrapped around tissue, edges (1113) of tubular structures (1115) can also be joined by externally placing 2 or more strips of backing of a MTDS device (1114) on approximated tissue as shown in the side views of FIGS. 11F–11G, and the axial view in FIG. 11H. The attachment points (1117) also point toward the area of tissue approximation (1116).

Figure 11I:
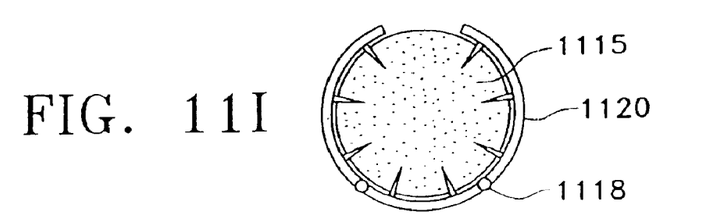
FIG. 11I is an axial view of a hinge in the backing of a device.
Figure 11J:
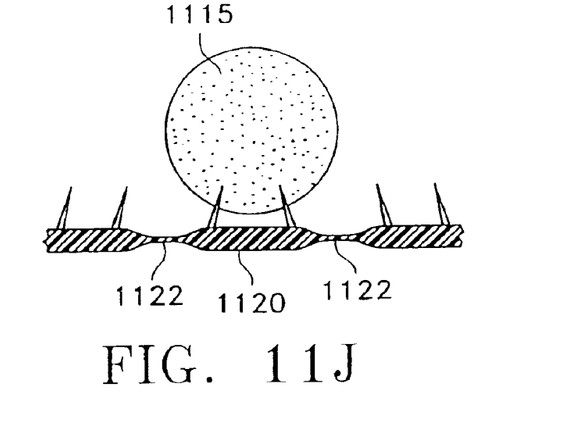
FIGS. 11J–11K are axial views of decreased backing material that are areas of enhanced device flexibility.
Figure 11K:
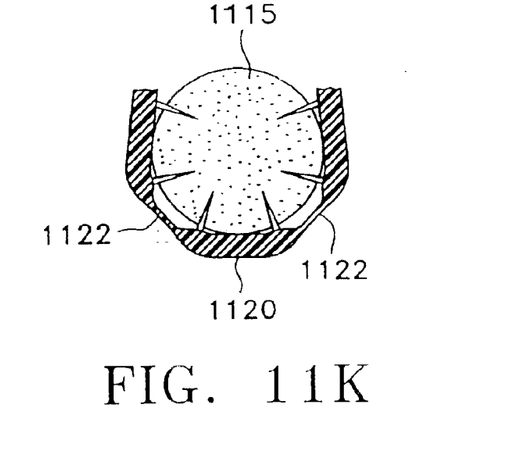
Figure 11L:
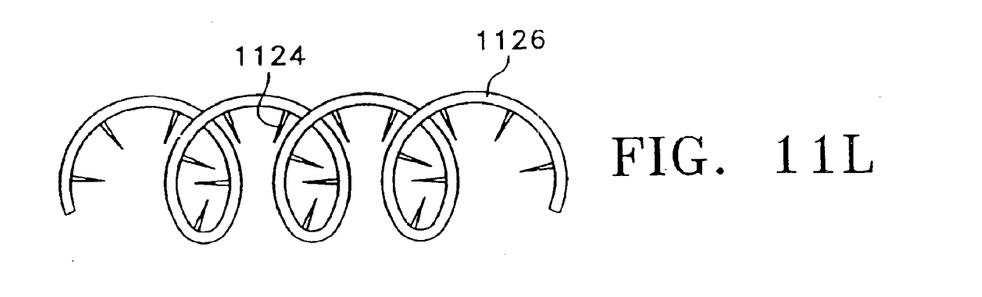
FIGS. 11L–11M are side views of a spring or coil-like MTDS device being used to approximate tissue.
Figure 11M:
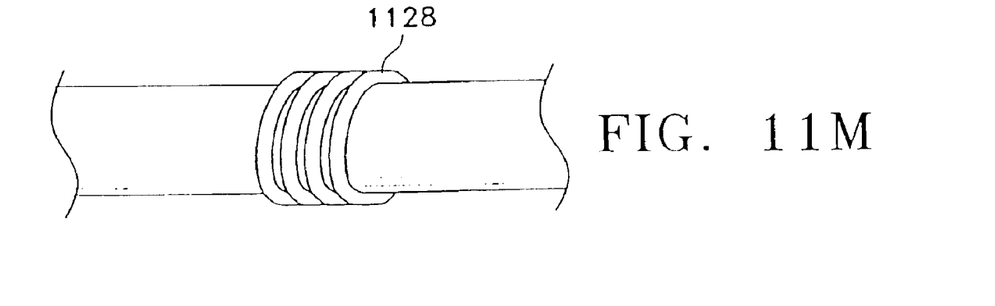

FIGS. 11I–11M are additional variations of the invention which vary the mechanisms used to improve device flexibility. In FIGS. 11I–11K, the backing has areas of comparatively higher flexibility than other areas of the backing. In an axial view of the variation in FIG. 11I, the backing is equipped with hinges (1118) that allow bending of the backing (1120) around tubular soft tissue structures (1115). In a second variation, the amount of material in the areas of the device that fold (1122) is reduced as shown in FIGS. 11J–11K. Another variation is seen in FIGS. 11L–11M where attachment points (1124) of a device extend from a backing in the form of a coil or spring (1126). The edges of soft tissue are approximated when the coil or spring is reduced (1128).

Figure 12A:
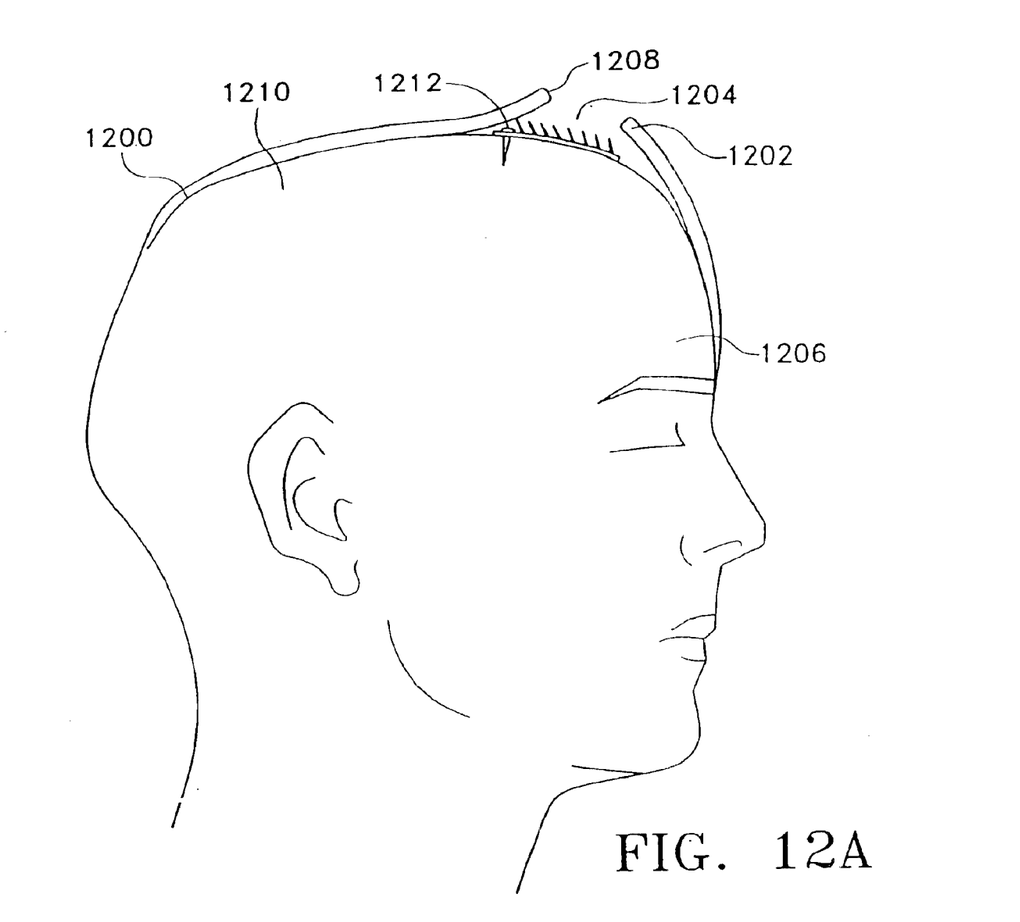
FIG. 12A is a schematic view of the MTDS device being used in a brow-lift procedure.
Figure 12B:
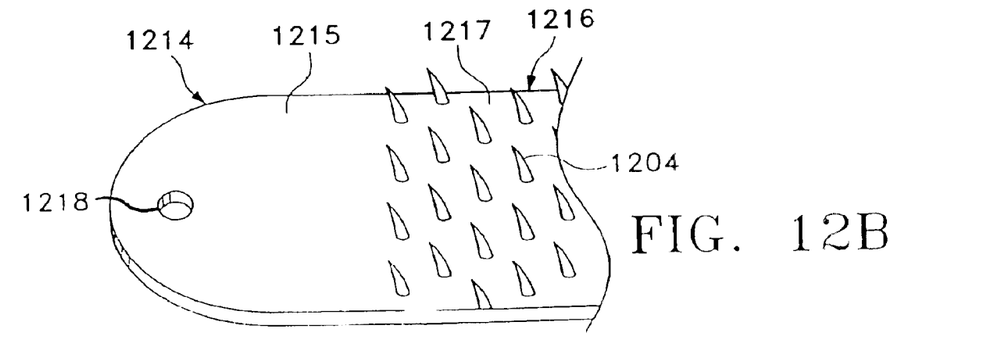
FIG. 12B is a plan, perspective view of the MTDS device used in a brow-lift.

The MTDS device may also be used in soft-tissue remodeling, such as a brow-lift, shown in FIG. 12A. After dissection of the scalp (1200), the anterior scalp flap (1202) may be raised over the attachment points (1204) to lift the brow (1206). The ends of both the anterior flap (1202) and posterior flap (1208) may then be trimmed and fixed onto the attachment points (1204) to close the wound. The device may be secured to the skull (1210) by a screw (1212). The inventive device in this example may have a first end (1214) and a second end (1216), the first end having a first area (1215) and the second end having a second area (1217). The first area (1215) and second area (1217) may have extending attachment points (1204) or one or more openings (1218) to accommodate a screw(s) (1212). The second area attachment points are canted toward the first end of the device as shown in FIG. 12B.

We have described this invention by example and by description of the physical attributes and benefits of the structure. This manner of describing the invention should not, however, be taken as limiting the scope of the invention in any way.

I claim as my invention:

1. An implantable device for placement on a tissue surface and interior to an exterior tissue surface comprising:
    a) a biodegradable supportive backing comprising a first biodegradable material, the supportive backing having:
        i.) at least a first area with a plurality of biodegradable attachment points extending from the first area for attaching to a selected tissue, wherein the plurality of attachment points is comprised of at least a second biodegradable material that is different than the first biodearadable material, and
        ii.) a second area discrete from the first area, wherein the backing has physical characteristics sufficient to approximate or to support the selected tissue adjacent the first area with respect to the second area, and
    b) the plurality of biodegradable attachment points extending from the first area, wherein the plurality of biodegradable attachment points are configured to attach to the selected tissue and to distribute tension between the first area and the selected tissue.

2. The implantable device of claim 1 wherein the first biodegradable material is more flexible than the second biodegradable material.

3. The implantable device of claim 1 wherein the first biodegradable material comprises a first polymer or copolymer and the second biodegradable material comprises a second polymer or copolymer.

4. The implantable device of claim 3 wherein said first polymer or copolymer comprises one or more materials selected from the group consisting of polyglycolide, polylactide, poly-α-caprolactone, polyglyconate, polylactide-co-glycolide, their mixtures, alloys, and random and block copolymers.

5. The implantable device of claim 3 wherein said second polymer or copolymer comprises one or more materials selected from the group consisting of polyglycolide, polylactide, poly-α-caprolactone, polyglyconate, polylactide-co-glycolide, their mixtures, alloys, and random and block copolymers.

6. The implantable device of claim 1 wherein the plurality of attachment points is additionally comprised of a plurality of biodegradable materials.

7. The implantable device of claim 1 wherein said plurality of biodegradable attachment points comprise more than one shape.

8. The implantable device of claim 1 wherein said plurality of biodegradable attachment points comprise shapes and directions selected from the group consisting of canted tines, erect tines, canted hooks, canted arrowheads, erect barbed tipped tines, canted barbed tipped tines, erect arrowhead tipped tines, canted arrowhead tipped tines, erect nail-shaped tines, canted nail-shaped tines, and cheese grater-like tines.

9. The implantable device of claim 1 wherein said biodegradable supportive backing comprises front and back sides.

10. The implantable device of claim 9 wherein said plurality of biodegradable attachment points extend from the biodegradable supportive backing on said front and back sides.

11. The implantable device of claim 10 wherein auxiliary biodegradable attachment points comprising a third biodegradable material extend from said back side.

12. The implantable device of claim 11 wherein the third biodegradable material comprises a third polymer or copolymer.

13. The implantable device of claim 12 wherein said third polymer or copolymer comprises one or more materials selected from the group consisting of polyglycolide, polylactide, poly-α-caprolactone, polyglyconate, polylactide-co-glycolide, their mixtures, alloys, and random and block polymers.

14. An implantable device for placement on a tissue surface and interior to an exterior tissue surface comprising:
   a) a supportive backing having:
      i.) at least a first biodegradable area with a plurality of biodegradable attachment points extending from the first area for attaching to a selected tissue and
      ii.) a second area discrete from the first area, wherein the backing has physical characteristics sufficient to approximate or to support the selected tissue adjacent the first area with respect to the second area, and
   b) the plurality of biodegradable attachment points extending from the first area, wherein the plurality of biodegradable attachment points are configured to attach to the selected tissue and to distribute tension between the first area and the selected tissue;
   wherein the first biodegradable area is comprised of a first biodegradable material and the plurality of biodegradable attachment points is comprised of a second biodegradable material that is different than the first biodegradable material.

15. The implantable device of claim 14 wherein the second area is biodegradable.

16. The implantable device of claim 14 wherein the second area comprises an anchor for tissue.

17. The implantable device of claim 16 wherein the anchor comprises a pin, nail, or screw.

18. The implantable device of claim 14 wherein the first biodegradable material comprises a first polymer or copolymer and the second biodegradable material comprises a second polymer or copolymer.

19. The implantable device of claim 18 wherein said first polymer or copolymer comprises one or more materials selected from the group consisting of polyglycolide, polylactide, poly-α-caprolactone, polyglyconate, polylactide-co-glycolide, their mixtures, alloys, and random and block copolymers.

20. The implantable device of claim 18 wherein said second polymer or copolymer comprises one or more materials selected from the group consisting of polyglycolide, polylactide, poly-α-caprolactone, polyglyconate, polylactide-co-glycolide, their mixtures, alloys, and random and block copolymers.

21. An implantable device for placement on a tissue surface and interior to an exterior tissue surface comprising:
   a) a biodegradable supportive backing having:
      i.) at least a first area having a first density with a plurality of biodegradable attachment points extending from the first area for attaching to a selected tissue and
   ii.) a second area discrete from the first area and having at least a second density that is different than the first density, wherein the backing has physical characteristics sufficient to approximate or to support the selected tissue adjacent the first area with respect to the second area, and
   b) the plurality of biodegradable attachment points extending from the first area, wherein the plurality of biodegradable attachment points are configured to attach to the selected tissue and to distribute tension between the first area and the selected tissue.

22. The implantable device of claim 21 wherein the first density is greater than the second density.

23. The implantable device of claim 21 wherein the first density is less than the second density.

24. The implantable device of claim 21 wherein the second area of the supportive backing additionally comprises a plurality of densities.

25. The implantable device of claim 21 wherein the first area having the first density comprises a first polymer or copolymer and the second area having the second density comprises a second polymer or copolymer.

26. The implantable device of claim 25 wherein said first polymer or copolymer comprises one or more materials selected from the group consisting of polyglycolide, polylactide, poly-α-caprolactone, polyglyconate, polylactide-co-glycolide, their mixtures, alloys, and random and block copolymers.

27. The implantable device of claim 25 wherein said second polymer or copolymer comprises one or more materials selected from the group consisting of polyglycolide, polylactide, poly-α-caprolactone, polyglyconate, polylactide-co-glycolide, their mixtures, alloys, and random and block copolymers.

* * * * *